(12) United States Patent
Takeuchi

(10) Patent No.: US 7,798,967 B2
(45) Date of Patent: Sep. 21, 2010

(54) ULTRASOUND DIAGNOSIS APPARATUS

(75) Inventor: Hideki Takeuchi, Mitaka (JP)

(73) Assignee: Aloka Co., Ltd., Tokyo (JP)

( * ) Notice: Subject to any disclaimer, the term of this patent is extended or adjusted under 35 U.S.C. 154(b) by 808 days.

(21) Appl. No.: 11/641,503

(22) Filed: Dec. 19, 2006

(65) Prior Publication Data

US 2008/0146930 A1 Jun. 19, 2008

(51) Int. Cl.
*A61B 8/00* (2006.01)
(52) U.S. Cl. .................. 600/447; 600/437; 600/440; 600/441; 600/443; 600/455; 600/456; 600/457; 600/458
(58) Field of Classification Search ............ 600/437, 600/443, 447, 459
See application file for complete search history.

(56) References Cited

U.S. PATENT DOCUMENTS

| | | | |
|---|---|---|---|
| 5,229,933 A | 7/1993 | Larson, III | |
| 5,349,262 A | 9/1994 | Grenon et al. | |
| 5,563,346 A | 10/1996 | Bartelt et al. | |
| 5,617,862 A | 4/1997 | Cole et al. | |
| 5,832,923 A | 11/1998 | Engeler et al. | |
| 5,897,501 A | 4/1999 | Wildes et al. | |
| 5,997,479 A | 12/1999 | Savord et al. | |
| 6,013,032 A | 1/2000 | Savord | |
| 6,089,096 A | 7/2000 | Alexandru et al. | |
| 6,102,863 A | 8/2000 | Pflugrath et al. | |
| 6,111,816 A | 8/2000 | Chiang et al. | |
| 6,120,449 A | 9/2000 | Snyder et al. | |
| 6,120,450 A * | 9/2000 | Li ............................. | 600/447 |
| 6,174,286 B1 | 1/2001 | Ramamurthy et al. | |
| 6,183,419 B1 | 2/2001 | Wildes | |
| 6,193,663 B1 | 2/2001 | Napolitano et al. | |
| 6,279,399 B1 | 8/2001 | Holm | |
| 6,375,617 B1 | 4/2002 | Fraser | |
| 6,419,633 B1 | 7/2002 | Robinson et al. | |
| 6,464,638 B1 * | 10/2002 | Adams et al. ............... | 600/443 |
| 6,475,150 B2 * | 11/2002 | Haddad ..................... | 600/448 |
| 6,491,634 B1 | 12/2002 | Leavitt et al. | |
| 6,524,254 B2 | 2/2003 | Erikson | |

(Continued)

FOREIGN PATENT DOCUMENTS

EP  1 491 914 A2  12/2004

(Continued)

OTHER PUBLICATIONS

U.S. Appl. No. 10/869,127.

*Primary Examiner*—Brian Casler
*Assistant Examiner*—Baisakhi Roy
(74) *Attorney, Agent, or Firm*—H. Henry Koda; William L. Androlia

(57) ABSTRACT

In an ultrasound diagnosis apparatus, a plurality of sub arrays are defined on a 2D array transducer. A plurality of groups are defined for each sub array. Each group is basically composed of a plurality of transducer elements which are connected in parallel with each other. A sub array shape is variably defined for a plurality of sub arrays in accordance with the beam direction and the depth of a focal point. Further, a grouping pattern is variably defined for each sub array. The acoustic distances between the respective transducer elements and the focal point is made as equal as possible for a plurality of transducer elements forming each group, whereby a preferable beam profile can be obtained.

4 Claims, 15 Drawing Sheets

U.S. PATENT DOCUMENTS

| | | |
|---|---|---|
| 6,537,219 B2 | 3/2003 | Poland et al. |
| 6,537,220 B1 * | 3/2003 | Friemel et al. ............... 600/447 |
| 6,540,862 B1 | 4/2003 | Calvert et al. |
| 6,582,367 B1 | 6/2003 | Robinson et al. |
| 6,676,602 B1 | 1/2004 | Barnes et al. |
| 6,868,729 B2 | 3/2005 | Amemiya |
| 7,090,642 B2 | 8/2006 | Satoh |
| 7,207,943 B2 * | 4/2007 | Barnes et al. ............... 600/447 |
| 7,217,243 B2 * | 5/2007 | Takeuchi .................... 600/447 |
| 7,322,936 B2 * | 1/2008 | Takeuchi .................... 600/447 |
| 7,534,209 B2 * | 5/2009 | Abend et al. ................ 600/454 |
| 2003/0018260 A1 | 1/2003 | Erikson |
| 2003/0188582 A1 | 10/2003 | Amemiya |
| 2005/0228277 A1 | 10/2005 | Barnes et al. |
| 2005/0243812 A1 | 11/2005 | Phelps |

FOREIGN PATENT DOCUMENTS

| | | |
|---|---|---|
| JP | 9-322896 | 12/1997 |
| JP | 10-267904 | 10/1998 |
| JP | 2000-33087 | 2/2000 |
| JP | 2000-254120 | 9/2000 |
| JP | 2000-300553 | 10/2000 |
| JP | 2001-104303 | 4/2001 |
| JP | 2001-276064 | 10/2001 |
| JP | 2001-286467 | 10/2001 |
| JP | 2003-290228 | 10/2003 |
| JP | 2004-105257 | 4/2004 |
| JP | 2005-34633 | 2/2005 |
| JP | 2005-34634 | 2/2005 |

* cited by examiner a, b, c : BELONGING TO R1, R2, AND R3
d, e, f : BELONGING TO R1, R2, AND R4
g, h, i : BELONGING TO R2, R3, AND R4
j, k, l : BELONGING TO R1, R3, AND R4

ULTRASOUND DIAGNOSIS APPARATUS

BACKGROUND OF THE INVENTION

1. Field of the Invention

The present invention relates to an ultrasound diagnosis apparatus for use in the field of medical treatment, and more particularly to setting of a plurality of sub arrays on an array transducer.

2. Description of Related Art

Ultrasound diagnosis apparatuses are used in the field of medical treatment for the purpose of diagnosing diseases of a living body (a patient). More specifically, ultrasonic diagnosis apparatuses transmit an ultrasonic pulse to a living body and receive a reflected wave therefrom for forming an ultrasonic image based on a receiving signal obtained by the reflected wave received.

A two-dimensional (2D) array transducer (or transducer array) is used for effecting two-dimensional scanning of ultrasonic beams to thereby form a three-dimensional echo data acquisition space within a living body. A 2D transducer is generally composed of a plurality of transducer elements arranged along X and Y directions.

In some 2D array transducers, a plurality of sub arrays are defined on the 2D array transducer for the purpose of channel reduction of a transmission/reception section, simultaneous formation of a plurality of reception beams, or like purposes. Conventionally, a plurality of sub arrays are fixedly defined on the 2D array transducer. For example, a plurality of sub arrays having a rectangular shape are set with respect to a 2D array transducer, and in this case, the shape of each sub array cannot be changed. Japanese Patent Laid-Open Publication No. 2001-276064 discloses grouping of a plurality of transducer elements in which the structure of each group is fixed. Japanese Patent Laid-Open Publication No. 2001-104303 discloses a structure for performing phase adjusting and summing (or beam formation) in two stages. Japanese Patent Laid-Open Publication No. Hei 9-322896 discloses, in FIG. 6, that a plurality of groups are fixedly set for a 2D array transducer, that a plurality of first beam formers are connected to the plurality of groups, and that a plurality of second beam formers are provided at a stage subsequent to the plurality of first beam formers. U.S. Pat. No. 5,832,923 discloses that a plurality of 2D sub arrays are defined on a 2D array transducer and that a plurality of groups are defined on each sub array. None of these documents, however, describes dynamically changing the shape of each sub array and the grouping patterns.

When the shape of the sub array or the grouping pattern is defined uniformly or fixedly, there arises a problem of the inability to obtain a beam profile preferable for specific transmission and reception wave conditions. For example, side lobes may tend to be generated in a specific beam scanning direction. European Patent Laid-Open Publications EP-1491913-A2 (corresponding to Japanese Patent Laid-Open Publication No. 2005-34634) and EP-1491914-A2 (corresponding to Japanese Patent Laid-Open Publication No. 2005-34633) disclose that a plurality of sub arrays are set on the array transducer and that a plurality of groups are set for each sub array. In this technique, each group is basically composed of a plurality of transducer elements, and a common transmission signal is supplied to the plurality of transducer elements. A plurality of reception signals supplied from the plurality of transducer elements forming each group are summed together, and a resultant reception signal obtained by summing is subjected to a delay process. European Patent Laid-Open Publication EP-1491913-A2 listed above further describes changing of the shape of each sub array in accordance with the beam scanning direction. None of these documents, however, describes dynamically changing the grouping pattern in accordance with the depth of a focus point.

In order to achieve an excellent focus, desirably, the structure of each group (i.e. the grouping pattern within each sub array) is set such that, for a plurality of transducer elements forming each group, which are connected in parallel with each other (i.e., have the same delay time), acoustic distances between a focal point and the respective transducer elements are made as equal as possible. The acoustic distance from the focal point to each transducer element changes with the beam address and the depth of the focal point (e.g., a transmission focal point). It is therefore desired to dynamically change the shape of the sub array and the grouping pattern in accordance with such a change in the beam scanning conditions.

SUMMARY OF THE INVENTION

The present invention advantageously provides an ultrasound diagnosis apparatus capable of providing an excellent beam profile.

The present invention advantageously maintains or improve image quality of an ultrasonic image when channel reduction of a transmission/reception section is performed.

(1) An ultrasound diagnosis apparatus according to one aspect of the present invention comprises an array transducer composed of a plurality of transducer elements for forming an ultrasonic beam which is to be scanned two-dimensionally; a switching section which is connected to the array transducer, the switching section defining a plurality of sub arrays with respect to the array transducer and defining a plurality of groups each composed of one or a plurality of transducer elements with respect to each sub array; a transmitter section which is connected to the array transducer via the switching section, for generating a group transmission signal for each group; and a receiver section which is connected to the array transducer via the switching section, for processing a reception signal of each group which is output from the switching section, wherein the switching section defines a grouping pattern individually for each sub array in accordance with at least a depth of a focal point.

With the above structure, the switching section has a function of defining a plurality of sub arrays on the array transducer and a function of defining a grouping pattern (i.e., an arrangement of a plurality of groups) for each sub array. The switching section can define the grouping pattern individually for each sub array and also can change the grouping pattern dynamically. Consequently, with regard to a plurality of transducer elements forming each group, the acoustic distances between the focal point and respective transducer elements within each group can be adjusted so as to equalize the distances as much as possible within a three-dimensional space, thereby realizing excellent focus. Specifically, by defining the grouping pattern in consideration of the depth of the focal point (i.e. the spatial focal position), an excellent beam profile can be obtained. Here, the focal point basically refers to a transmission focal point, and the above-described ultrasonic beam is a transmission beam. With regard to the reception beam, applying dynamic focus technology is desirable. Although in principle each group is composed of a plurality of transducer elements, a single transducer element may form a group. Preferably, the number of transducer elements forming each group and the form of a group can be varied in accordance with the depth of the focal point. As will be described below, although changing the sub array shape in accordance with the beam scanning conditions (particularly the beam scanning direction), the sub array shape may be fixed.

Preferably, the switching section dynamically changes the grouping pattern defined for each sub array, in the course of scanning the ultrasonic beam. As such, it is possible to simultaneously define a plurality of types of grouping patterns, rather than a uniform grouping pattern, with respect to the plurality of sub arrays as a whole.

Preferably, the switching section further defines the grouping pattern individually for each sub array in accordance with the position of each sub array in consideration of a beam address. The beam address specifies the beam direction. In general, the beam direction is defined by the position of a beam passing through a horizontal plane which is orthogonal to the vertical center axis of the array transducer, or is defined by the beam deflecting angle with respect to the vertical center axis of the array transducer and the beam rotation angle. Alternatively, the sub array address may be referred to so as to specify the position of each sub array. At the time of control by the switching section, information which indirectly represents the beam address or the like, rather than information representing the beam address or the like, may be referred to. Further, at the time of such control, it is desirable to use a table for generating a grouping pattern set including the grouping patterns for the respective sub arrays when the beam address and the depth of the focal point are input. The sub array address may be provided to the table as further input data.

Preferably, the switching section has a function of distributing and outputting the group transmission signal to a plurality of transducer elements forming the corresponding group and a function of summing a plurality of reception signals from a plurality of transducer elements forming each group and generating a group receipt signal for each group.

A plurality of sub arrays are preferably closely coupled with each other closely on the array transducer in consideration of their acoustic power or sensitivity. In other words, desirably, all the effective transducer elements forming the array transducer belong to one of the sub arrays. However, an interval may be formed between the sub arrays. In other words, there may be ineffective transducer elements which do not belong to any sub array and do not function in transmission and receipt. Further, such an ineffective transducer element which does not function in transmission and receipt may be provided within the sub array.

For example, when n groups are set with respect to m transducer elements forming a certain sub array (1<n<m), a channel reduction ratio of n/m is achieved. By performing such a channel reduction process within the probe head, the number of signal lines inserted through the probe cable can be advantageously reduced. With such grouping, a plurality of reception signals are summed and combined into a single reception signal (a group reception signal). Further, a single transmission signal (a group transmission signal) can be supplied in parallel to a plurality of transducer elements forming one group.

Although in principle each group is composed of a plurality of transducer elements, a single transducer element may form a group. Preferably, the number of transducer elements forming each group in one sub array is not uniform and is dynamically variable. Preferably, on the array transducer, a pattern variable region is defined for each sub array, whereby a plurality of pattern variable regions are defined on the array transducer, the pattern variable region for each sub array corresponding to a region formed by combining a plurality of sub array shape patterns concerning the respective sub array, and the plurality of pattern variable regions partially overlapping each other. Preferably, each pattern variable region covers a plurality of transducer elements peculiar to the respective sub array and a plurality of transducer elements existing on a portion where the plurality of pattern variable regions partially overlap.

(2) An ultrasound diagnosis apparatus according to another aspect of the present invention comprises an array transducer composed of a plurality of transducer elements for forming an ultrasonic beam which is to be scanned two-dimensionally; a switching section which is connected to the array transducer, the switching section defining a plurality of sub arrays with respect to the array transducer in accordance with a beam address and a depth of a focal point and defining, with respect to each sub array, a plurality of groups each being composed of one or a plurality of transducer elements in accordance with a position of each sub array; a transmitter section which is connected to the array transducer via the switching section, for generating a group transmission signal for each group; and a receiver section which is connected to the array transducer via the switching section, for processing a reception signal of each group which is output from the switching section.

With the above structure, by setting the sub array shapes for a plurality of sub arrays and the grouping pattern with respect to each sub array, an excellent ultrasonic beam can be formed, to thereby increase the quality of an ultrasonic image. In particular, since the sub array shape can be changed appropriately, side lobes can be reduced.

Preferably, at the period of scanning the ultrasonic beam, the switching section dynamically changes the sub array shape defined for each sub array and also dynamically changes the grouping pattern defined for each sub array. Preferably, the switching section changes the sub array shape defined for each sub array in accordance with the beam scanning direction on a horizontal plane which is orthogonal to the vertical center axis of the array transducer.

Preferably, after a sub phase adjusting and summing process is performed for each group, a main phase adjusting and summing process is applied to a plurality of sub phase adjusted and summed signals. Here, a plurality of main phase adjusting and summing circuits may be disposed in parallel for simultaneously forming a plurality of receiving beams by means of a single receiving process. Further, in the probe cable, a transmission signal may be transmitted in the form of a voltage signal and a reception signal may be transmitted in the form of a current signal. The transmission signal may be a signal of approximately 100V, or may be a low voltage signal of several to tens of V. In the latter case, each transducer element is desirably formed in, for example, a laminate structure, to thereby lower electrical impedance of each transducer element.

Preferably, at least the array transducer and the switching section are provided within the probe head. Further, a plurality of sub phase adjusting and summing circuits may be provided within the probe head (in this case, the number of signal lines can be further reduced), or a plurality of sub phase adjusting and summing circuits may be provided within the probe connector or the apparatus body. The transmitter section can be provided in the probe head, the cable connector, or the apparatus body. Further, an intermediate device may be provided between the probe head and the probe connector, with the plurality of sub phase adjusting and summing circuits and the transmitter section being provided within the intermediate device.

BRIEF DESCRIPTION OF THE DRAWINGS

These and other objects of the invention will be explained in the description below, in connection with the accompanying drawings, in which.

DESCRIPTION OF PREFERRED EMBODIMENTS

Preferred embodiments of the present invention will be described with reference to the drawings.

Figure 1:
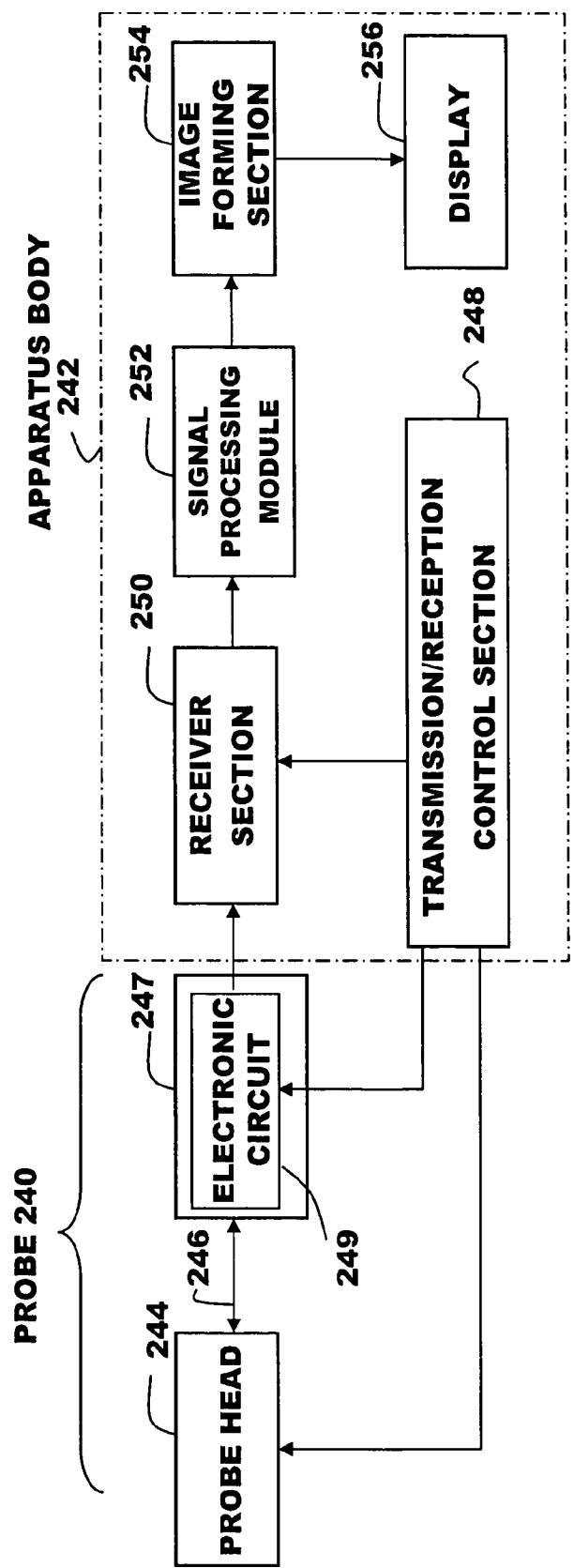
FIG. 1 is a block diagram showing the overall structure of an ultrasound diagnosis apparatus according to an embodiment of the present invention.

Referring first to FIG. 1, a basic structure of an ultrasound diagnosis apparatus according to a first embodiment of the present invention will be described. The ultrasound diagnosis apparatus is composed of a probe (probe unit) 240 and an apparatus body 242. The probe 240 includes a probe head 244, a probe cable 246, and a cable connector 247. An intermediate device including a built-in electronic circuit 249 to be described below may be provided between the probe head 244 and the cable connector 247; i.e., in the middle of the probe cable 246. The apparatus body 242 includes a transmission/reception control section 248, a receiver section 250, a signal processing module 252, an image forming section 254, and a display 256. The cable connector 247 is detachably connected to a connector (not shown) of the apparatus body 242. In the present embodiment, the cable connector 247 includes the built-in electronic circuit 249, which performs a sub phase adjusting and summing process and a transmission signal generation process, as will be further described below with reference to FIGS. 2 and 3. The probe head 244 transmits and receives ultrasound. A receipt signal, which is obtained by transmission and receipt of ultrasound, is then input to the image forming section 254 via the electronic circuit 249, the receiver section 250, and the signal processing module 252. The image forming section 254 forms an ultrasonic image based on the signal received. The ultrasonic image is displayed on the screen of the display 256. Two-dimensional tomography images, two-dimensional bloodstream images, and three-dimensional images are known as ultrasonic images. In the present embodiment, volume data obtained from a three-dimensional space within a living body are subjected to a volume rendering process to form a three-dimensional image. Many other methods for forming a three-dimensional image are also known, and may be applied when preferable.

Figure 2:
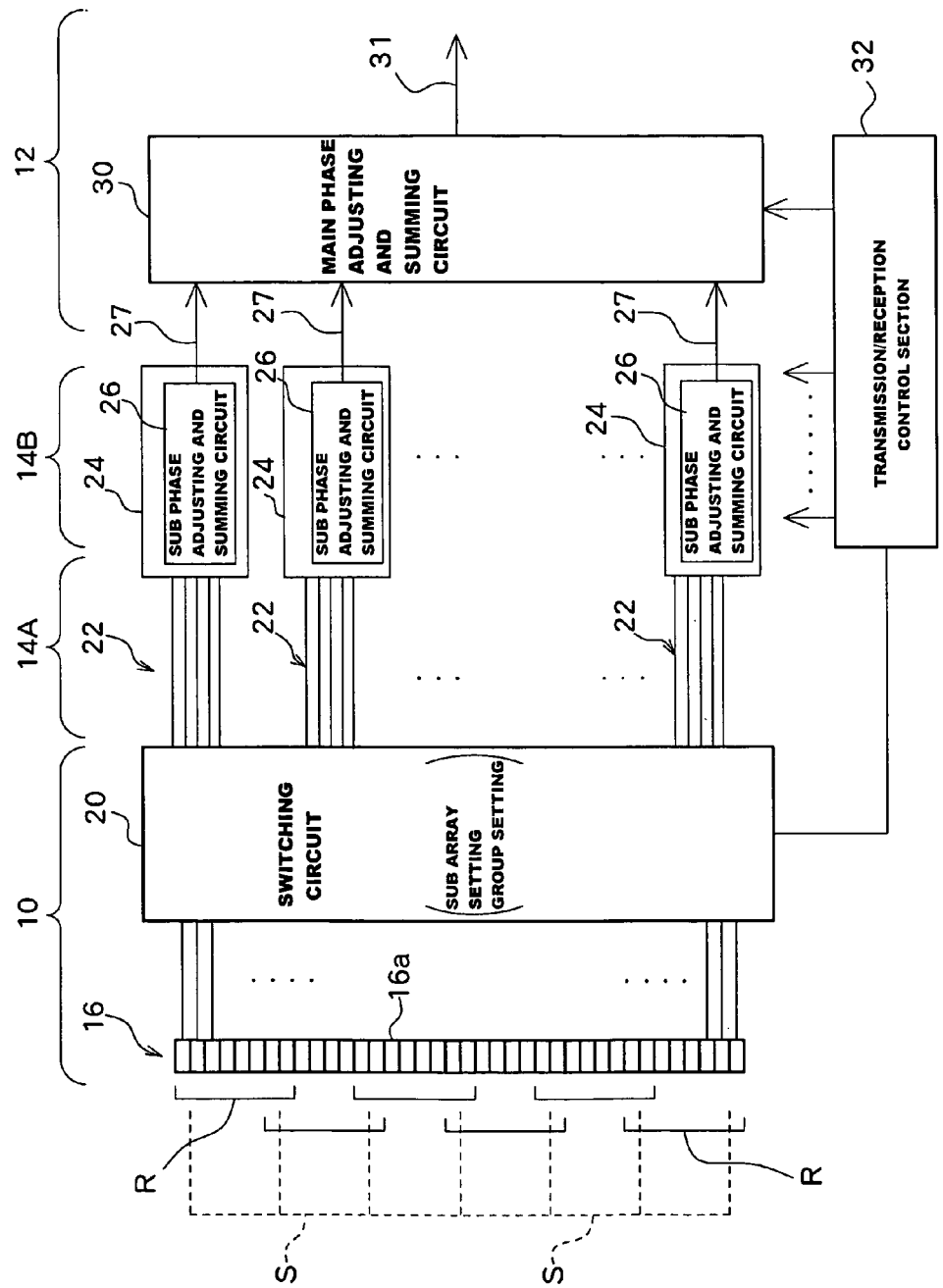
FIG. 2 is a block diagram showing a transceiver section in an ultrasound diagnosis apparatus according to the present invention.

FIG. 2 is a block diagram showing a structure of a transmitter/receiver (transceiver) section in an ultrasound diagnosis apparatus according to the embodiment. The ultrasound diagnosis apparatus as shown is composed of a probe unit and an apparatus body 12. The probe unit is composed of a probe head 10, a probe cable 14A, and a cable connector 14B.

In this embodiment, the cable connector 14B includes a plurality of transmission/reception modules 24 (corresponding to the electronic circuit 249 described above), which will be described below. However, the plurality of transmission/reception modules 24 may be provided within the probe head 10, the apparatus body 12, or the intermediate device described above.

The probe head 10, which is used in contact with a body surface, is, for example, a wave transmitter/receiver for effecting transmission and reception of ultrasound. The probe head 10 includes a 2D array transducer 16 which forms an ultrasonic beam. The ultrasonic beam is two-dimensionally scanned electronically, thereby forming a three-dimensional echo data acquisition space (a three-dimensional space). An example of the electronic scanning method of the ultrasonic beam is electronic sector scanning. Alternatively, there may be employed an electronic linear scanning method, an electronic convex scanning method, or the like.

In the present embodiment, the array transducer 16 is composed of a great number of (3000 or 4000, for example) transducer elements 16a which are arranged two-dimensionally, as will be described below with reference to FIG. 4.

A switching circuit 20 is formed in the form of a multiplexer or a switching matrix. In the present embodiment, the switching circuit 20 has a function of defining a plurality of sub arrays on the 2D array transducer 16 and a function of setting a plurality of groups for each sub array. The switching circuit 20 also has a function of changing a shape of each sub array (a sub array shape pattern) and a function of changing a shape of each group (a group shape pattern).

Particularly, in the present embodiment, as will be described in detail below with reference to FIGS. 13 to 15, the shape of each sub array is selected in accordance with the beam forming condition, and simultaneously the grouping pattern is defined individually for each sub array, so as to reduce side lobes and achieve an excellent beam profile. Specifically, with regard to a plurality of transducer elements forming one group, which are connected in parallel with each other (i.e. which have the same delay time), the acoustic distances between the respective transducer elements and the focal point are made as equal as possible, so that a phase shift among the plurality of transducer elements can be minimized. Also, in order to achieve this more appropriately, the sub array shape is varied. Although in the present embodiment, a uniform sub array shape is defined for a plurality of sub arrays, a plurality of sub arrays may differ in sub array shape. Here, the switching circuit 20 may be formed from a single circuit as shown in FIG. 2, or from a plurality of circuits.

In FIG. 2, a plurality of sub arrays S which are defined by the switching circuit 20 are conceptually shown. A plurality of sub arrays S are closely coupled with each other on the 2D array transducer 16, and in principle all the transducer elements 16a are used to form the plurality of sub arrays S. In the present embodiment, the shape of each sub array can be changed as described above, and the shape variable region for each sub array is conceptually shown and indicated by R in FIG. 2. Changing of the sub array shape will be described in detail below. A plurality of groups are set for each sub array, and the grouping pattern can be also changed freely. In the present embodiment, the number of transducer elements forming each group can be dynamically varied in accordance with the transmission/reception conditions, as will be detailed below.

In one example, regardless of which sub array shape is selected, each sub array is composed of 5×5=25 transducer elements, which are grouped or divided into 5 groups each including 5 transducer elements. As such, a channel reduction ratio of ⅕ is achieved within the probe head 10.

The terminals in the switching circuit 20 are equal in number to the transducer elements forming the 2D array transducer 16 on the side of 2D array transducer 16, and the series of terminals are equal in number to the sub arrays on the side of apparatus body 12. In the example shown in FIG. 2, each series of terminals provided on the side of the apparatus body 12 is composed of 5 terminals (that is, the terminals are equal in number to the groups set on a single sub array). More specifically, the switching circuit 20 selectively connects an array of element signal lines with an array of group signal lines. The array of group signal lines is composed of a plurality of sets of group signal lines 22, and in the example shown in FIG. 2, each set of group signal lines is composed of 5 group signal lines. The switching circuit 20 includes a plurality of switches (not shown) respectively provided at intersections between the array of element signal lines and the array of group signal lines. With the ON/OFF operation of each of these switches, one or a plurality of transducer elements to be connected with each group signal line are selected. The switching circuit 20 is capable of varying the number of transducer elements forming each group in accordance with the beam scanning direction (namely, the beam deflecting direction). The switching circuit 20 is also capable of setting one or a plurality of ineffective transducer elements (i.e., a transducer element which is not connected with any group signal line and does not effect transmission and reception of ultrasound) in accordance with the beam scanning direction. Further, each sub array may be composed of, for example, 4×4=16 transducer elements, which are grouped into 4 groups. Still further, the sub array and the group may be defined under other conditions.

As can be understood from the above description, the switching circuit 20 outputs 5 group reception signals for each sub array. A group reception signal is obtained, for example, by summing 5 reception signals output from 5 transducer elements forming each group. In the example used to illustrate this embodiment, the summing is achieved by a simple summing method using connection. More specifically, a plurality of reception signals are summed by interconnection of a plurality of signal lines. However, a weighted addition method or the like may be employed. The number of reception signals to be summed depends on the number of transducer elements forming a group. Meanwhile, as will be described below, 5 transmission signals are generated for each sub array within the cable connector 14B, and these 5 transmission signals are respectively supplied to 5 groups forming the corresponding sub array. Specifically, one transmission signal is distributed (supplied in parallel) to 5 transducer elements forming one group. Namely, within the switching circuit 20, one transmission signal is divided into 5 signals. Here, the number of signals obtained by division depends on the number of transducer elements forming one group.

As described above, reference numeral 22 indicates sets of signal lines provided for each sub array. Each set of signal lines 22 is composed of 5 signal lines (5 group signal lines). The above-described transmission signal and the reception signal are transmitted to each signal line. Here, it may be the case that the reception signal is transmitted in the form of a current signal and the transmission signal is transmitted in the form of a voltage signal. In this case, the transmission signal may be, for example, of approximately 100V, or a low voltage signal of approximately several V. The probe cable 14A also includes, in addition to the plurality of sets of signal lines 22, one or more control lines for transmitting a control signal or the like. In FIG. 2, a power line or the like inserted through the probe cable 14A is omitted.

The cable connector 14B has a box shape, for example, and contains therein a plurality of transmission/reception modules 24 as described above. Each transmission/reception module 24 includes a transmitter section and a sub phase adjusting and summing circuit (or a sub beam-former) 26. The transmitter section includes 5 transmitters, thereby generating 5 transmitting signals for each sub array. Further, the sub phase adjusting and summing circuit 26 performs a sub phase adjusting and summing process with respect to 5 group reception signals which are input thereto. With this process, a sub phase adjusted and summed signal 27 is generated for each sub array.

In the present embodiment, a main phase adjusting and summing circuit (or a main beam-former) 30 and a transmission/reception control section 32 are provided within the apparatus body 12. The main phase adjusting and summing circuit 30 receives a plurality of sub phase adjusted and summed signals 27 and subjects these signals to a main phase adjusting and summing process, thereby generating a main phase adjusted and summed signal (a receiving beam signal) 31. A known technology for dynamic focus in receiving can be applied to the phase adjusting and summing process. Each of the sub phase adjusting and summing circuits 26 and the main phase adjusting and summing circuit 30 may be formed as an analog phase adjusting and summing circuit or as a digital phase adjusting and summing circuit.

The transmission/reception control section 32 performs an operation control for each of the elements shown in FIG. 2; in particular, setting of a phase adjusting and summing condition in a plurality of sub phase adjusting and summing circuits 26 and setting of phase adjusting and summing conditions in the main sub phase adjusting and summing circuit 30. Further, the transmission/reception control section 32 outputs a control signal to the switching circuit 20 provided within the probe head 10. With this control signal, setting of a plurality of sub arrays and setting of a plurality of groups is performed. The transmission/reception control section 32 has an unillustrated switching circuit control table. This table is used to determine the connection condition in the switching circuit 20; i.e., the ON/OFF operation of switch groups for connecting a plurality of transducer elements forming the array transducer 16 and a plurality of group signal lines, in accordance with the beam address and the depth of the focal point. As such, with the beam address and the depth of the focal point being specified, a set of grouping patterns for the whole array transducer 16 (i.e., a plurality of sub array patterns and the grouping pattern for each sub array) can be determined by reference to the table. However, there may also be employed a table for generating a connection pattern for each sub array in accordance with the beam address, the depth of the focal point, and the sub array address, or another table.

Figure 3:
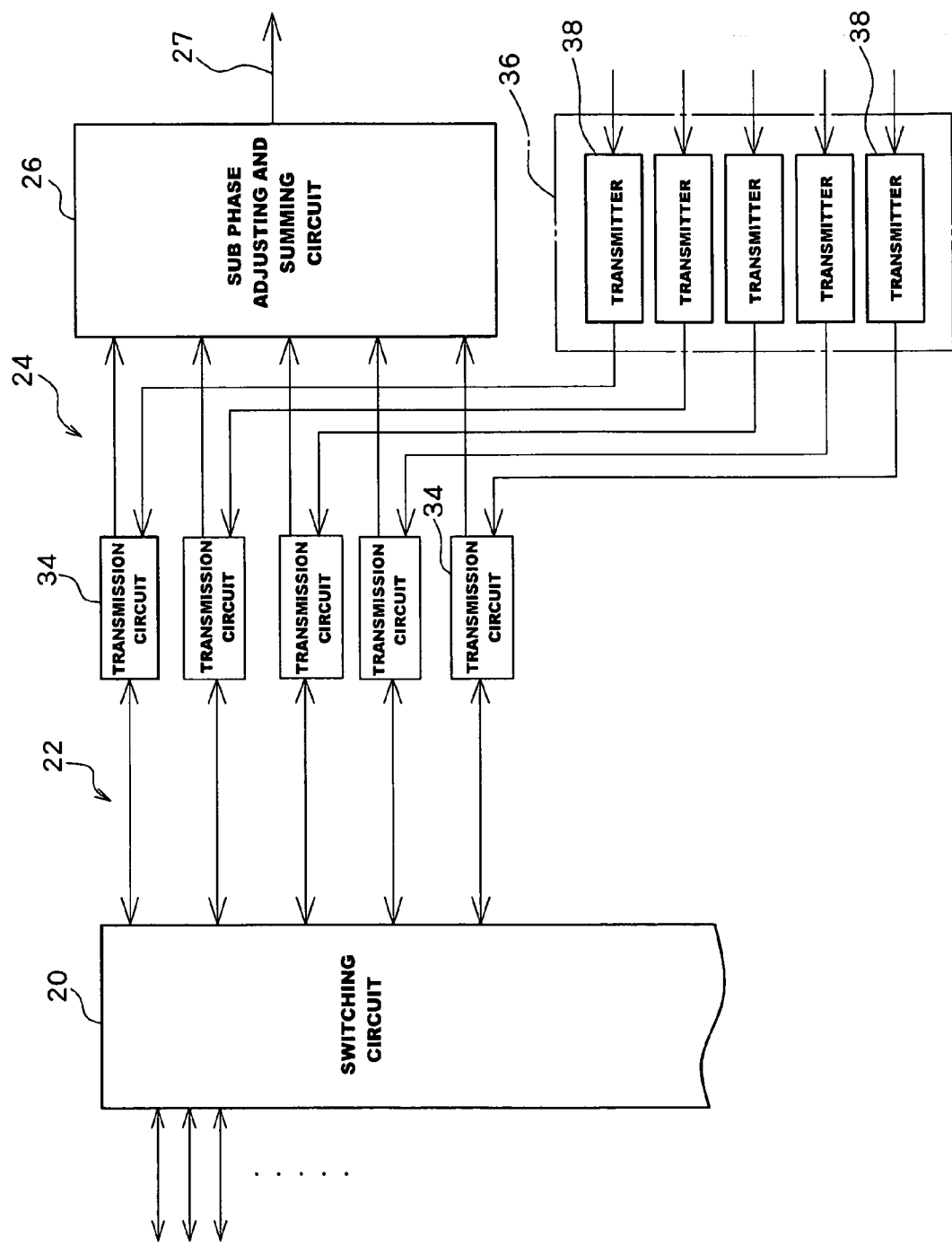
FIG. 3 is a block diagram showing a specific example structure of the transmission/reception module shown in FIG. 1.

FIG. 3 shows a specific example structure of the transmission/reception module 24 shown in FIG. 2. As described above, the transmission/reception module 24 includes a transmitter section 36, the sub phase adjusting and summing circuit 26, and a plurality of two-way transmission circuits (input-output circuits) 34. Here, each two-way transmission circuit 34 functions as a pulser for transmitting and as a head amp circuit for receiving. Each two-way transmission circuit 34 outputs a transmission signal to a signal line at the time of transmission and transmits a reception signal input from a signal line to the phase adjusting and summing circuit 26 at the time of reception. The transmitter section 36 is composed of 5 transmitters 38. Each transmitter 38 outputs a transmission signal to which a predetermined delay time is added.

The sub phase adjusting and summing circuit 26 described above may be formed as an analog phase adjusting and summing circuit having a delay line, for example, or as a digital phase adjusting and summing circuit functioning as a digital beam former. Further, the sub phase adjusting and summing circuit 26 may also be formed as a phase adjusting and summing circuit using a CCD device.

A variety of embodiments can be employed for the elements provided on the apparatus body side with respect to the switching circuit 20, and the structure shown in FIG. 1 is one of the examples.

The operation of the switching circuit 20 will be described with reference to FIGS. 4 to 10.

Figure 4:
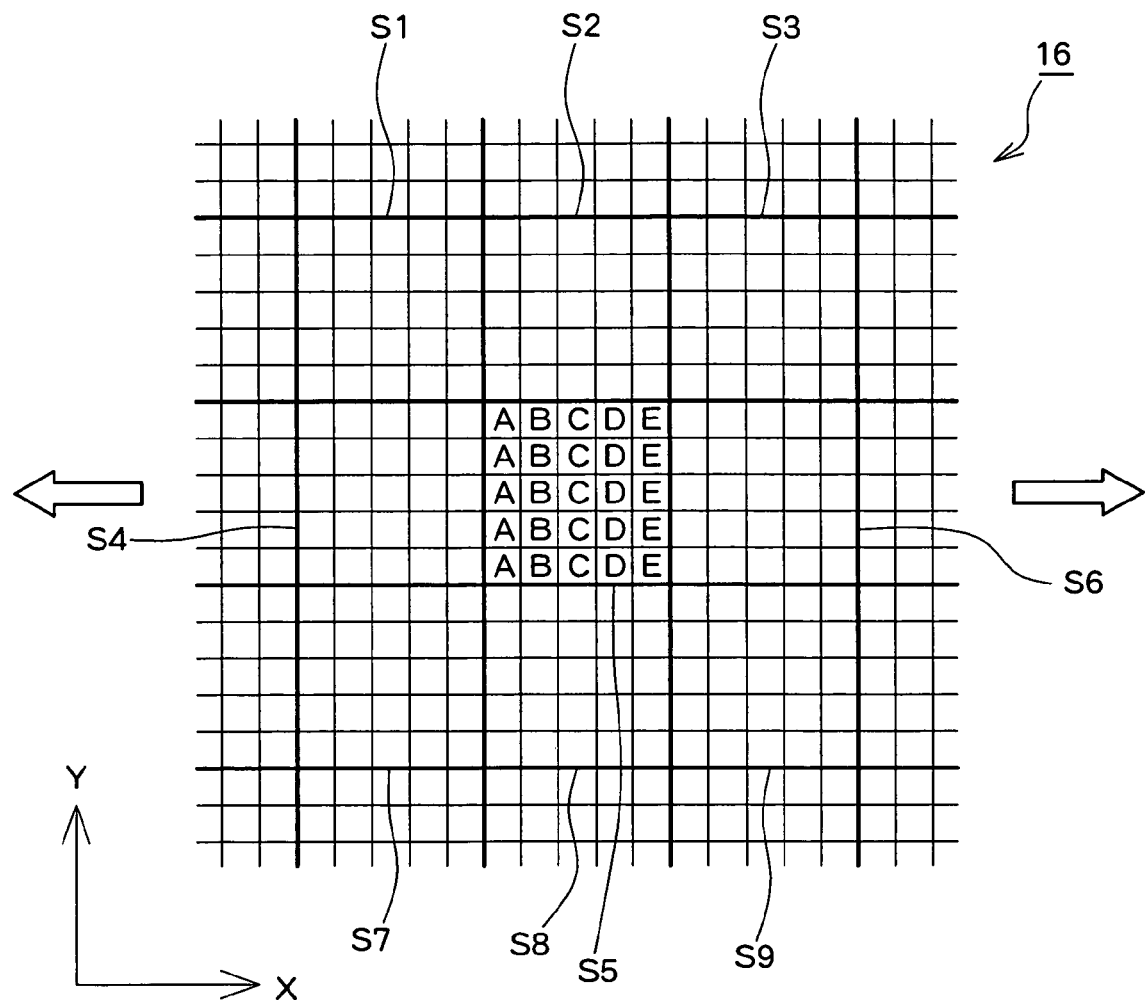
FIG. 4 is a view showing an example sub array shape.

FIG. 4 conceptually shows a portion of the 2D array transducer 16. Each cell corresponds to one transducer element. A plurality of sub arrays having a rectangular sub array shape are defined on the 2D array transducer 16. FIG. 4 particularly shows sub arrays S1 to S9, which are closely coupled with each other with no intervals therebetween. In FIG. 4, an example group setting method is shown, for reference, with regard to the sub array S5. In the example shown in FIG. 4, 5 groups are set in the X direction, and each group is composed of 5 transducer elements arranged along the Y direction. In FIGS. 4, A, B, C, D, and E are identifiers of the groups to which the respective transducer elements belong. This similarly applies to each of the drawings which will be described below. Assuming that the vertical center axis of the array transducer corresponds to the Z direction, the X direction and the Y direction as shown are orthogonal to the Z direction and correspond to two axes, respectively, which define a horizontal plane.

The sub array shape shown in FIG. 4 is the most common sub array shape, which is a square. The grouping pattern of each group shown in FIG. 4, which is a linear shape extending in the Y direction, is also common. This grouping pattern (the arrangement of a plurality of groups within the sub array) is adopted when an ultrasonic beam is scanned in the X direction as shown in FIG. 4, for example.

Figure 5:
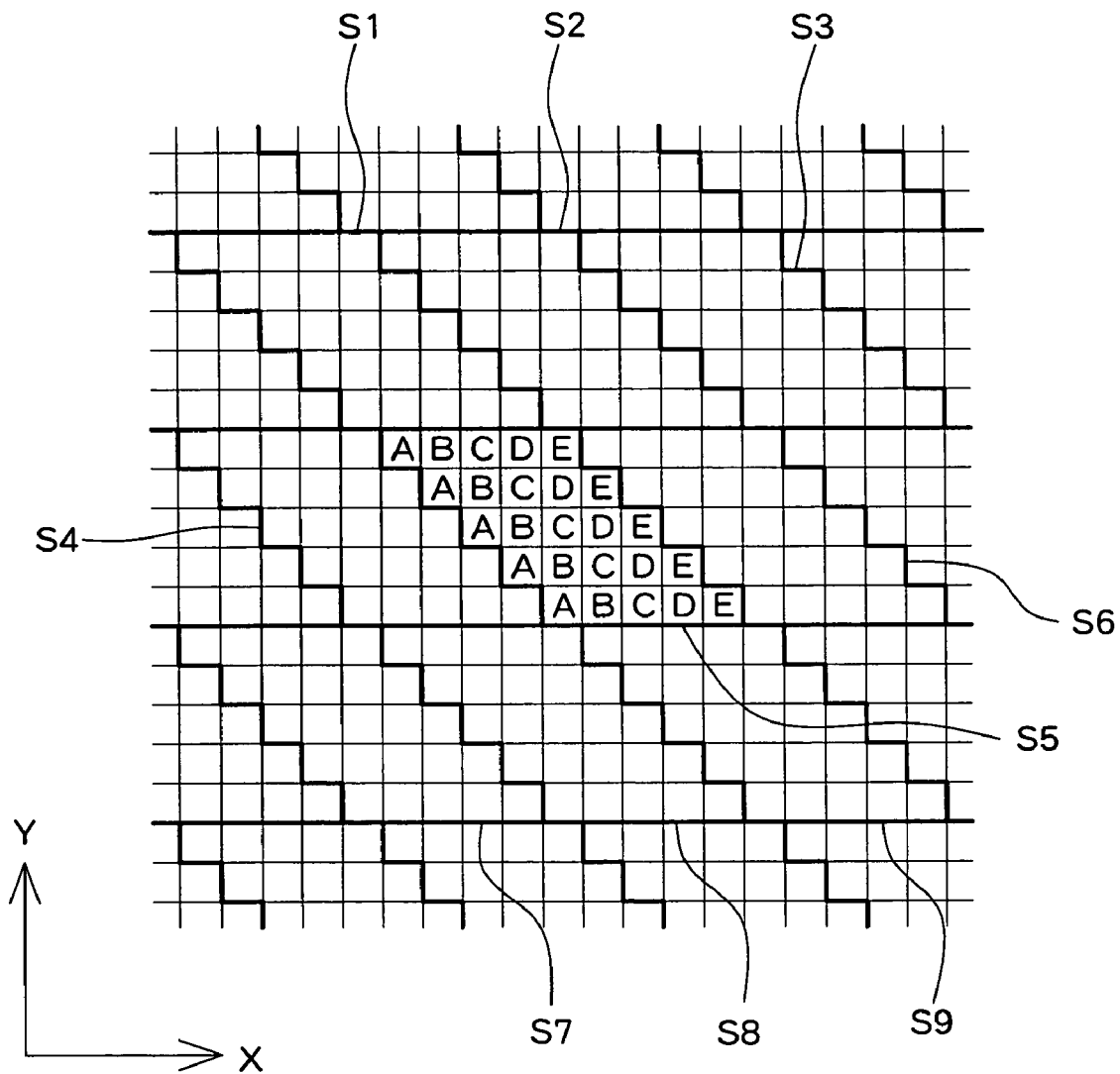
FIG. 5 is a view showing another example sub array shape.

FIG. 5 shows another example of the sub array shape. Each sub array S1 to S9 is slanted stepwise in the diagonal direction and has an overall parallelogram shape. With regard to the sub array S5, for example, the grouping as shown is achieved. Specifically, a group A is composed of 5 transducer elements which are linearly aligned diagonally. Each of the other groups has the same structure; the position of each transducer element in the X direction for each group is shifted in parallel by one step in the X direction at each stage in the Y direction. For other sub arrays, the same grouping pattern as that of the sub array S5 is used.

By adopting the sub array shape and the grouping pattern as shown in FIG. 5, when an ultrasonic beam is scanned in the direction which is slanted by 45 degrees with respect to the both X and Y directions at a certain focal point depth, the thickness of each group in that direction can be reduced to only $1/\sqrt{2}$ the thickness of the transducer element; namely, it becomes possible to prevent a problem that the apparent width of the transducer portion increases in the beam scanning direction. This will be described in detail. In the present embodiment, the same delay time is added on group units. In other words, a plurality of transducer elements forming each group are connected in parallel at the time of transmission and reception, and they form a single transducer portion as a whole. When the width of such a transducer portion increases in the beam scanning direction, side lobes might increase in size. On the other hand, when the sub array shape and the grouping pattern are appropriately defined as shown in FIG. 5, it is possible to prevent an apparent increase in the width of the transducer portion. In other words, the above-noted problems can be solved or mitigated.

Figure 6:
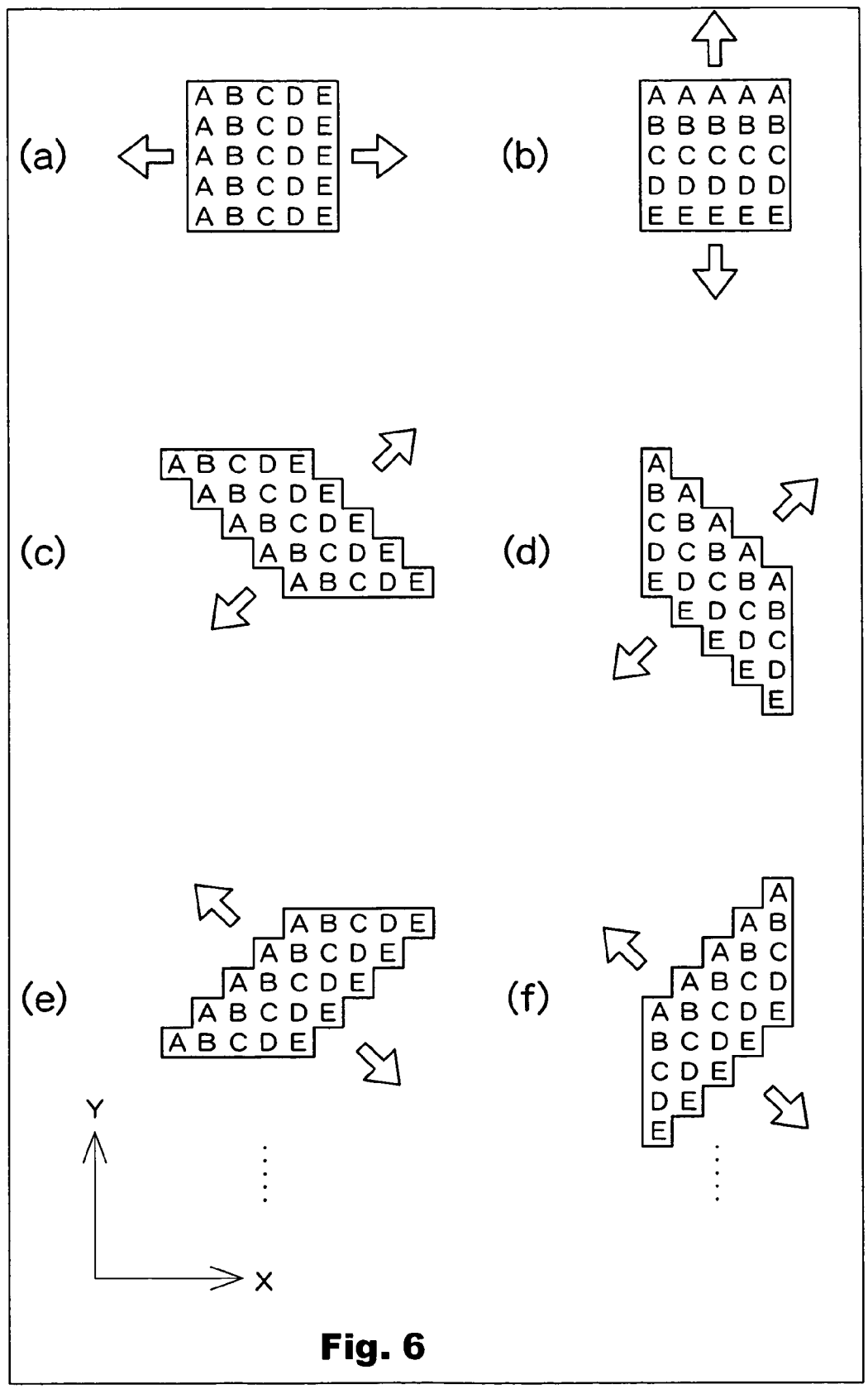
FIG. 6 is a view for explaining a plurality of sub array shapes by means of comparison.

FIG. 6 shows various types of sub array shapes and grouping patterns. The sub array shape shown in FIG. 6(*a*) is the same as that shown in FIG. 4 and is used when scanning an ultrasonic beam in the X direction. The sub array shape shown in FIG. 6(*b*) is the same as that shown in FIG. 6(*a*) with respect to the outer shape, but has a different grouping pattern within the sub array. More specifically, in FIG. 6(*b*), 5 groups are arranged in the Y direction, and each group is composed of 5 transducer elements arranged in the X direction. This pattern is adopted when scanning an ultrasonic beam in the Y direction.

FIG. 6(*c*) shows a sub array shape which is the same as that shown in FIG. 5. The sub array shape pattern shown in FIG. 6(*d*) is obtained by shifting the sub array shape shown in FIG. 6(*b*) stepwise in the X direction by one step at each stage in the Y direction. The sub array shape shown in FIG. 6(*d*), as well as that shown in FIG. 6(*c*), is preferable when scanning an ultrasonic beam upward and to the right (downward and to the left) with respect to the sheet plane.

The sub array shape shown in FIG. 6(*e*) has a shape obtained by deforming the sub array shape pattern shown in FIG. 6(*c*) in the opposite diagonal direction. This sub array shape is preferable when scanning an ultrasonic beam upward and to the left (downward and to the right) with respect to the sheet plane.

The sub array shape pattern shown in FIG. 6(*f*) has a shape obtained by deforming the sub array shape pattern shown in FIG. 6(*d*) in the opposite diagonal direction. This sub array shape, similar to that shown in FIG. 6(*e*), is preferable when scanning an ultrasonic beam upward and to the left (downward and to the right) with respect to the sheet plane.

Obviously, these sub array shapes or the like shown in FIG. 6 are merely illustrative, and a variety of other sub array shapes can be adopted. Specifically, the sub array shape (and the grouping pattern) is desirably set in accordance with the beam forming condition, particularly the beam scanning direction and the focus depth, so as to prevent side lobes as much as possible; namely, so as to obtain a better beam profile. Here, in order to simplify the structure of the switching circuit 20 and also facilitate control thereof, the number of selectable sub array shapes may be limited to approximately 4, for example. In this case, the sub array shapes shown in FIG. 6(*a*), (*b*), (*c*) (or (*d*)), and (*e*) (or (*f*)) can be adopted.

Figure 7:
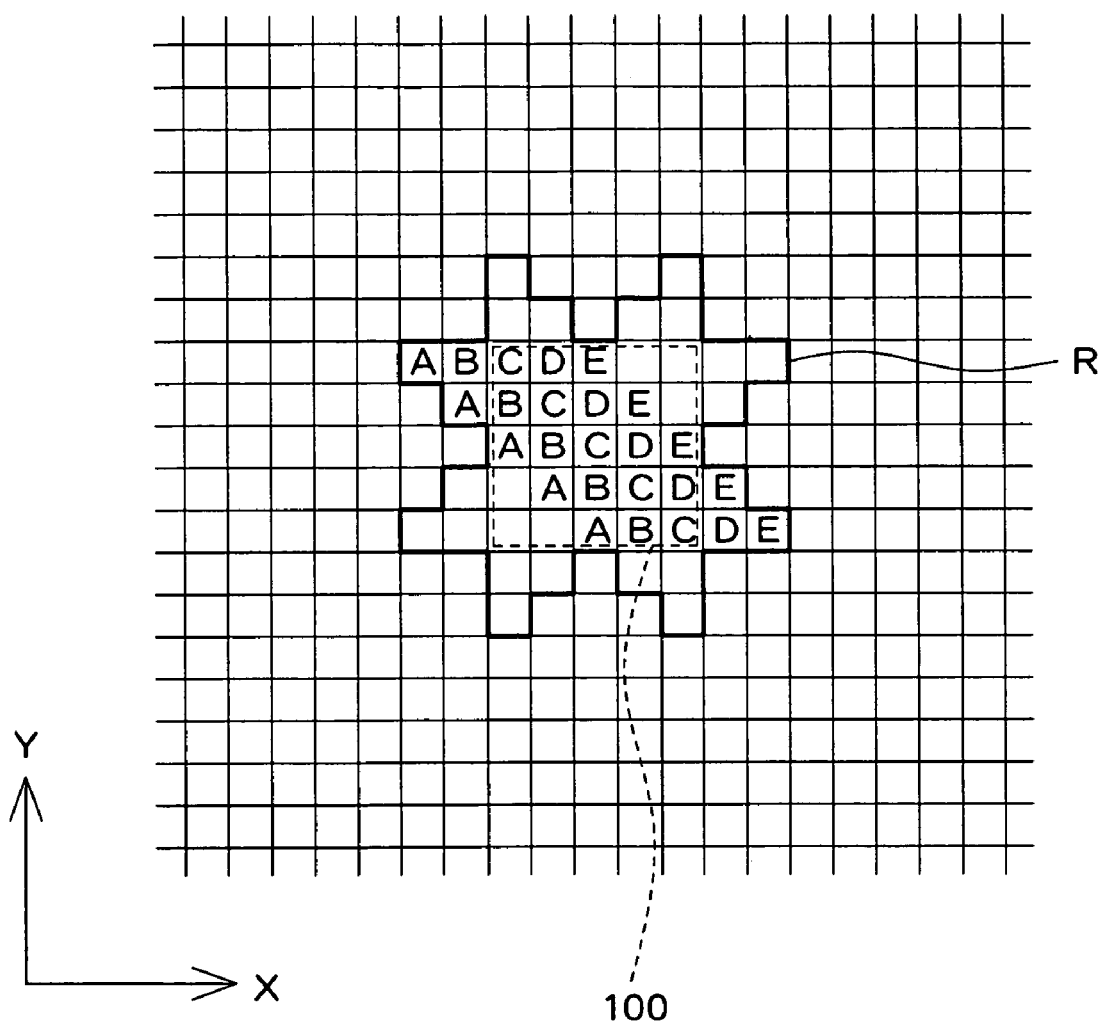
FIG. 7 is a view illustrating a variable range existing for each sub array.

In FIG. 7, a variable region R regarding one specific sub array is indicated with a bold line. This variable region is defined by the largest outer edge of a region which the certain sub array can have when the sub array shape changes. Therefore, the variable region R corresponds to a region obtained by superposing the shapes shown in FIGS. 6(a) to (f). In FIG. 7, reference numeral 100 indicates the most basic sub array shape, which is a square. Further, the grouping pattern shown in FIG. 6(c) is used, for reference, in the example of FIG. 7.

As can be understood from the shape of the variable region R shown in FIG. 7, a plurality of adjacent variable regions R partially overlap each other. At each transmission and reception process, however, adjacent sub arrays are closely coupled with each other and do not overlap each other. Overlapping of the variable regions will be described with reference to FIG. 8.

Figure 8:
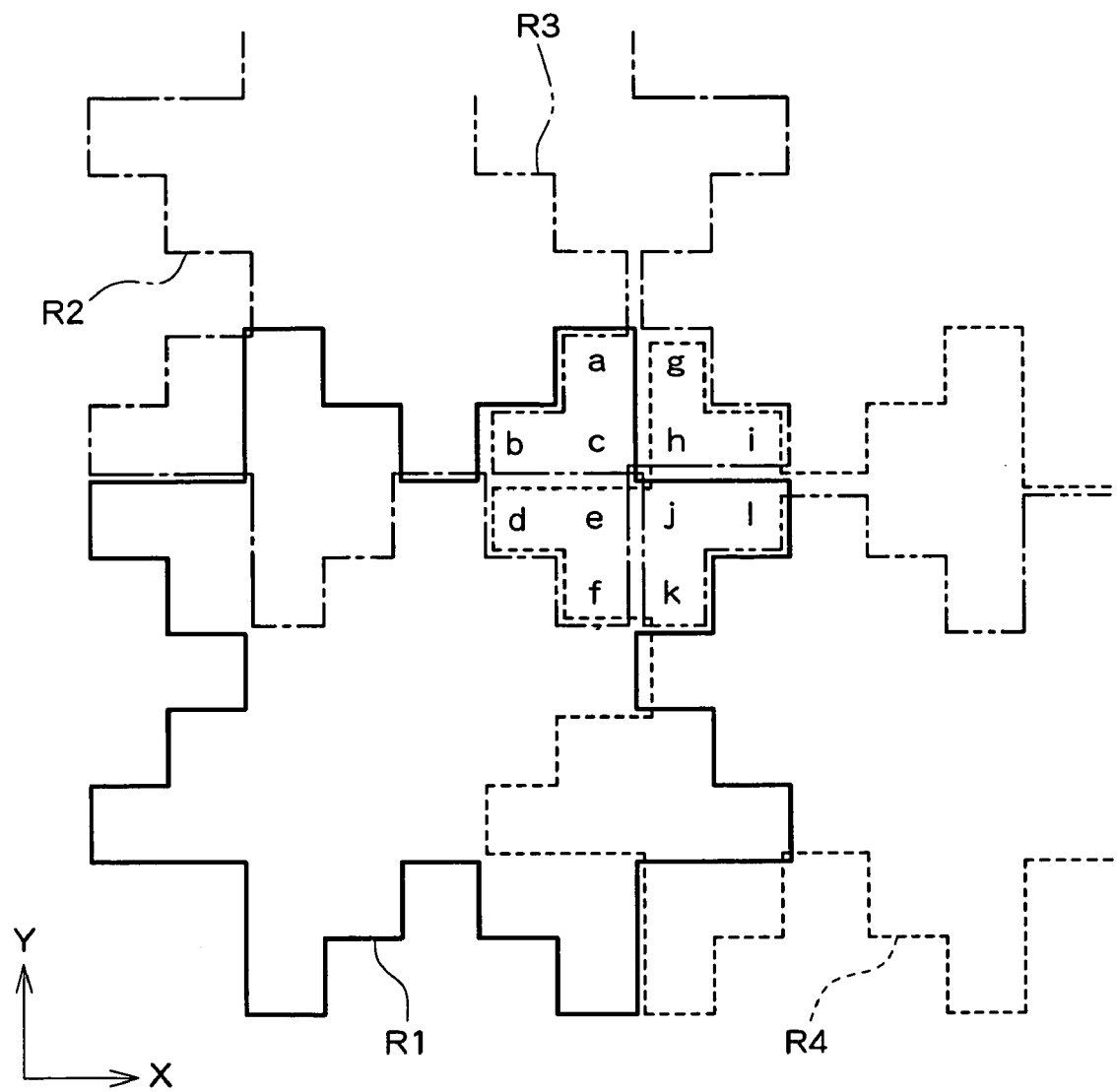
FIG. 8 is a view for explaining overlapping among a plurality of variable regions.

Referring to FIG. 8, R1 to R4 show 4 variable regions concerning 4 sub arrays, respectively, arranged adjacently in the upper-lower and right-left directions. Here, the variable region R1 is indicated by a solid line, the variable region R2 is indicated by an alternate long-and-short dashed line, the variable region R3 is indicated by an alternate long-and-two short dashed line, and the variable range R4 is indicated by a broken line.

The transducer elements a to l located in the portion where these variable regions partially overlap each other will be explained. The transducer elements a, b, and c belong to the variable regions R1, R2, and R3; the transducer elements d, e, and f belong to the variable regions R1, R2, and R4; the transducer elements g, h, and i belong to the variable regions R2, R3, and R4; and the transducer elements j, k, and l belong to the variable regions R1, R3, and R4.

Focusing on the variable region R1, the transducer elements a to f and j to l are included within the variable region R1 (whereas the transducer elements g to i are not included), and the variable region R1 also includes a plurality of transducer elements peculiar to the variable region R1. These peculiar transducer elements include 13 transducer elements, which are disposed close to each other in a diamond shape about the center of the variable region R1.

Figure 9:
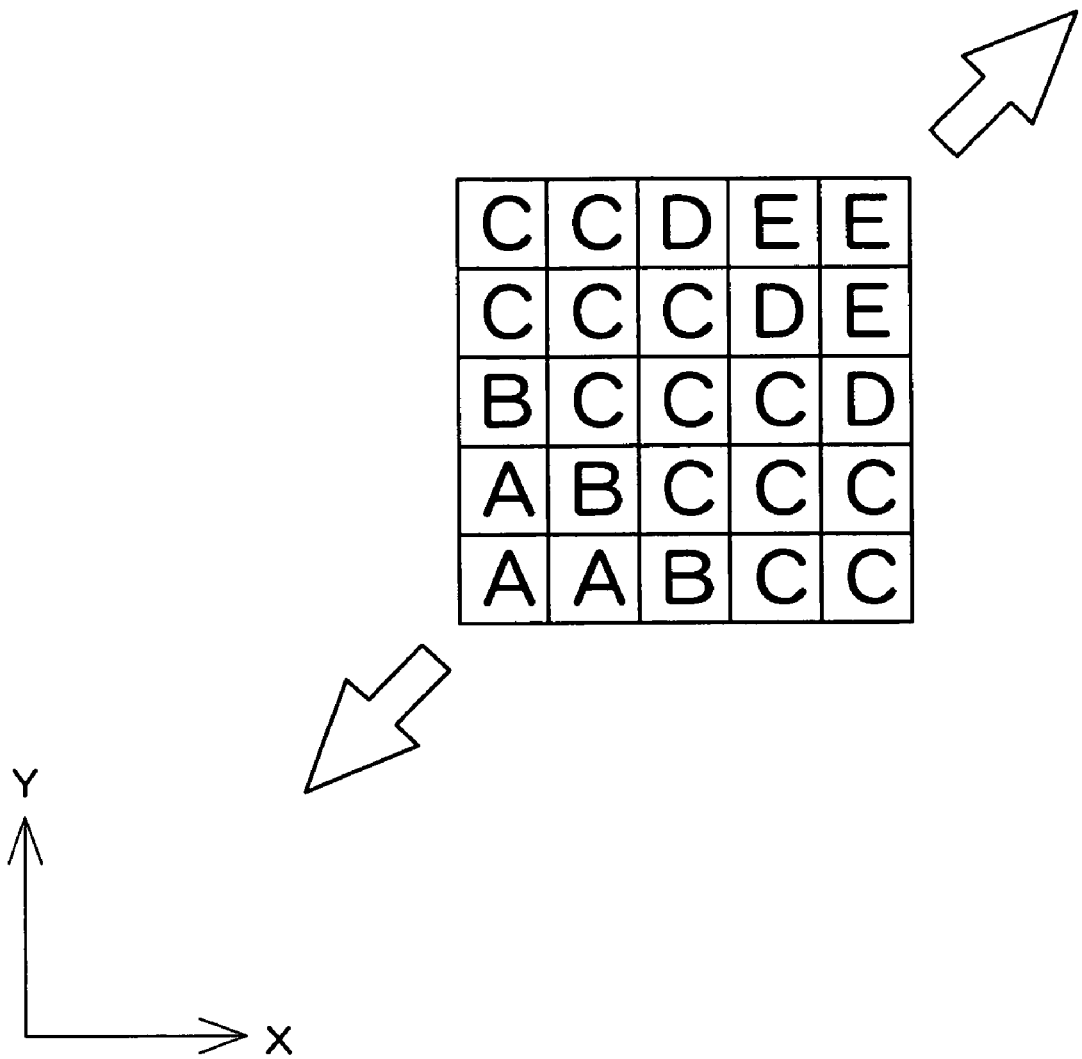
FIG. 9 is a view for explaining a comparative example.

FIG. 9 shows a comparative example. In this example, the sub array has a fixed square shape. The grouping pattern as shown in FIG. 9, for example, is set when scanning an ultrasonic beam in the diagonal direction. Here, this grouping pattern is also fixed. In this case, a plurality of transducer elements belonging to the group C exist along the beam scanning direction (that is, the thickness of the transducer portion C is increased in that direction), which results in deformation of ultrasonic beam profile, leading to easy generation of side lobes. According to the present embodiment, on the other hand, with the dynamical setting of the sub array shape and the grouping pattern, a problem which is caused in the case as shown in FIG. 9 can be solved or mitigated, as will be described below.

Figure 10:
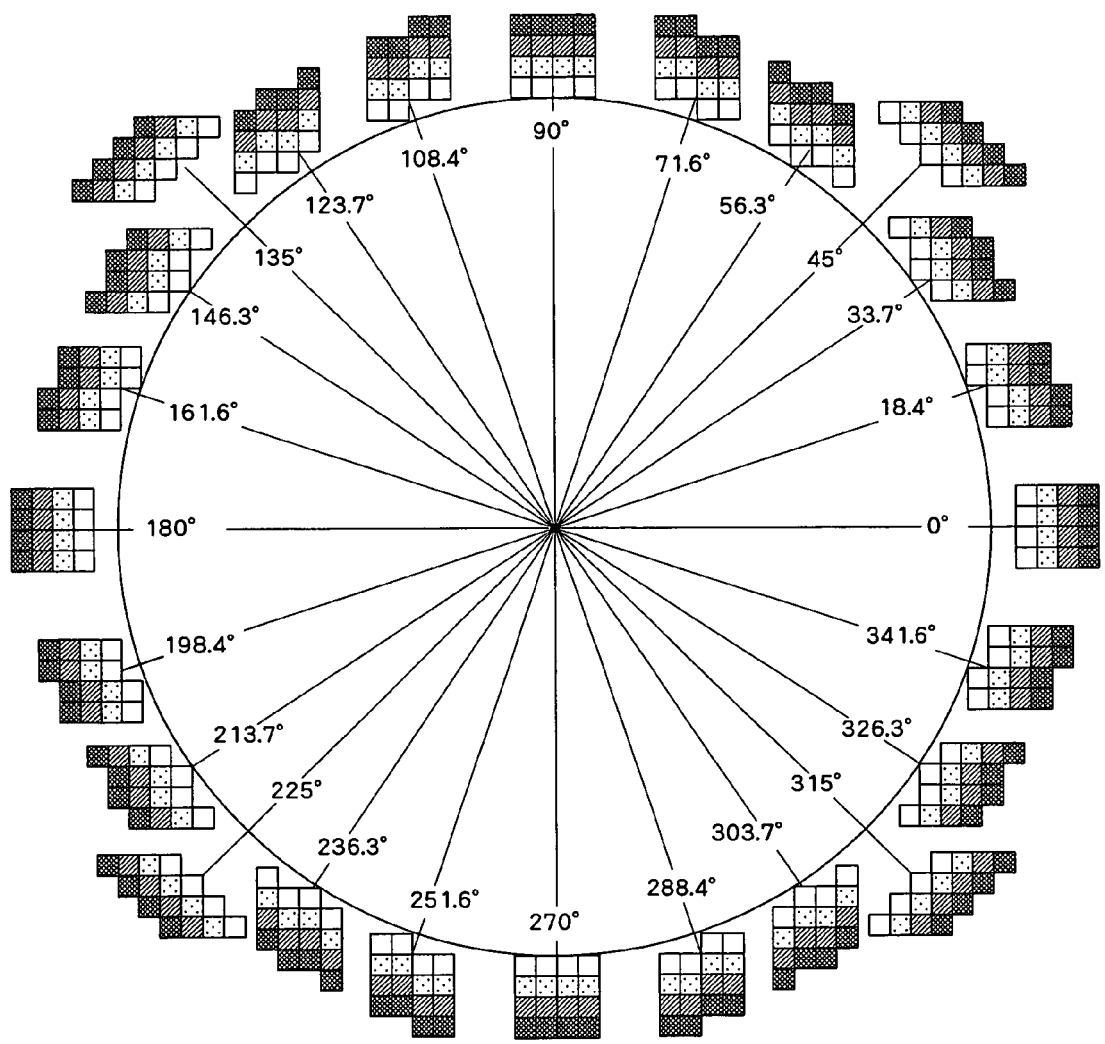
FIG. 10 is a view showing various sub array shapes according to another embodiment of the present invention.

FIG. 10 shows another example concerning the sub array shape, in which one sub array is composed of 4×4=16 transducer elements. As shown in FIG. 10, 16 transducer elements forming each sub array are grouped into 4 groups. In FIG. 10, each group is hatched in a different manner for the purpose of identification. The numerical values shown in FIG. 10 indicate the angles representing the scanning direction of an ultrasonic beam (corresponding to the beam rotation angle about the vertical axis). It should be noted that each grouping pattern shown in FIG. 10 is illustrative, and a variety of grouping patterns can actually be defined selectively for each sub array shape in accordance with the transmission and reception conditions.

By adaptively changing each sub array shape (and the grouping pattern simultaneously) in accordance with the scanning direction of an ultrasonic beam as shown in FIG. 10, a preferable beam profile can be obtained in any beam direction. A plurality of sub arrays can be closely coupled with each other regardless of which sub array shape shown in FIG. 10 is adopted. When the scanning direction is 45 degrees, for example, a plurality of sub arrays are closely coupled to each other without any intervals therebetween, as shown in FIG. 5. With regard to other scanning angles, a plurality of sub arrays are similarly coupled closely with each other.

At an end portion of a 2D array transducer, however, one or a plurality of transducer elements which substantially do not function may exist. Further, although in the above embodiment no interval is formed between a plurality of sub arrays, it is possible to provide between adjacent sub arrays one or a plurality of transducer elements which substantially do not function sub array.

The variable setting method of the sub array shape as described above is also applicable to a 1.5D array transducer in which a plurality of transducer elements are arranged two-dimensionally, in addition to a 2D array transducer.

Figure 11:
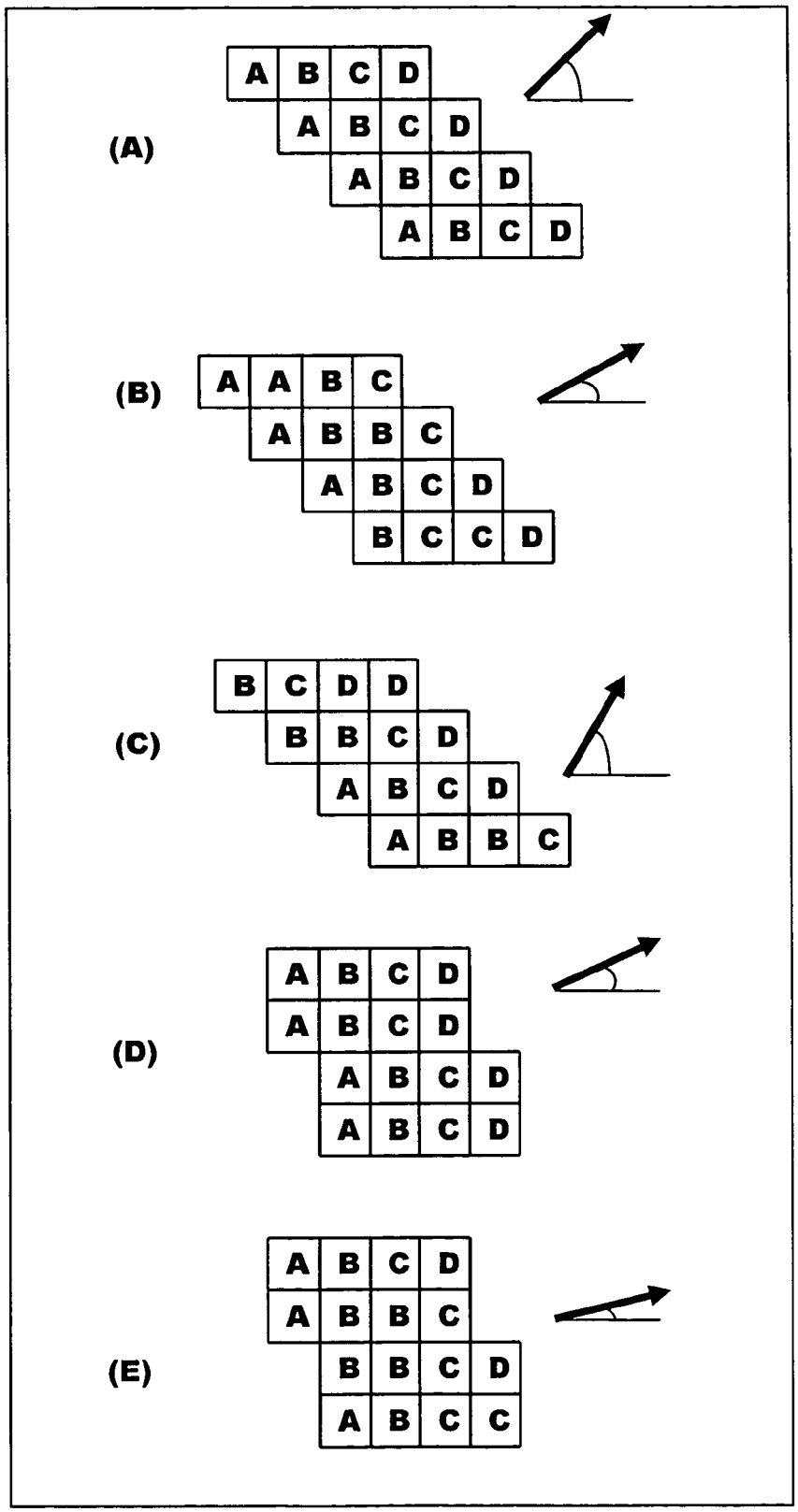
FIG. 11 is a view for explaining an embodiment in which the number of transducer elements varies from group to group.

Additional variations for changing the sub array shape and the grouping pattern will be described with reference to FIGS. 11 and 12. In FIG. 11, the sub array is composed of 4×4 transducer elements.

FIG. 11(A) shows a sub array shape when the beam scanning direction is 45 degrees. Each group is composed of 4 transducer elements arranged orthogonally with respect to the beam scanning direction (indicated by a bold arrow), and each group has the same shape. FIG. 11(B) shows a sub array shape when the beam scanning direction is smaller than 45 degrees. While the sub array shown in FIG. 11(B) has the same sub array shape (outer shape) as the sub array shown in FIG. 11(A), the number of transducer elements forming a group differs among a plurality of groups, and the groups A, B, and C have non-linear shapes in FIG. 11(B). FIG. 11(C) shows a sub array shape when the beam scanning direction is greater than 45 degrees. Although the sub array shown in FIG. 11(C) has the same sub array shape as the sub array shown in FIG. 11(A), the number of transducer elements forming a group differs among a plurality of groups, and the groups B, C, and D have non-linear shapes in FIG. 11(C). FIG. 11(D) shows another sub array shape when the beam scanning direction is smaller than 45 degrees. The sub array shown in FIG. 11(D) has a sub array shape which is different from that shown in FIG. 11(A). In FIG. 11(D), the group shape is identical for a plurality of groups. FIG. 11(E) shows a sub array shape when the beam scanning direction has a considerably small angle. Although the shape of the sub array shown in FIG. 11(E) is the same as that of the sub array shown in FIG. 11(D), the number of transducer elements forming a group is not identical among a plurality of groups. Regardless of which sub array shape is adopted, a plurality of sub arrays can be closely coupled with each other.

As described above, by changing both the sub array shape and the grouping pattern in accordance with the beam scanning direction, a preferable ultrasonic beam can be formed. In particular, by varying the number of transducer elements forming each group in accordance with the beam scanning direction, side lobes can be reduced more effectively.

Although in the above embodiment, all of a plurality of transducer elements forming each sub array function as effective transducer elements (transducer elements effecting transmission and reception of ultrasound), one or a plurality of ineffective transducer elements (transducer elements not effecting transmission and reception of ultrasound) may be provided within each sub array when the beam scanning direction corresponds to a predetermined angle. A further embodiment, configured in this manner, will be described below with reference to FIG. 12.

Figure 12:
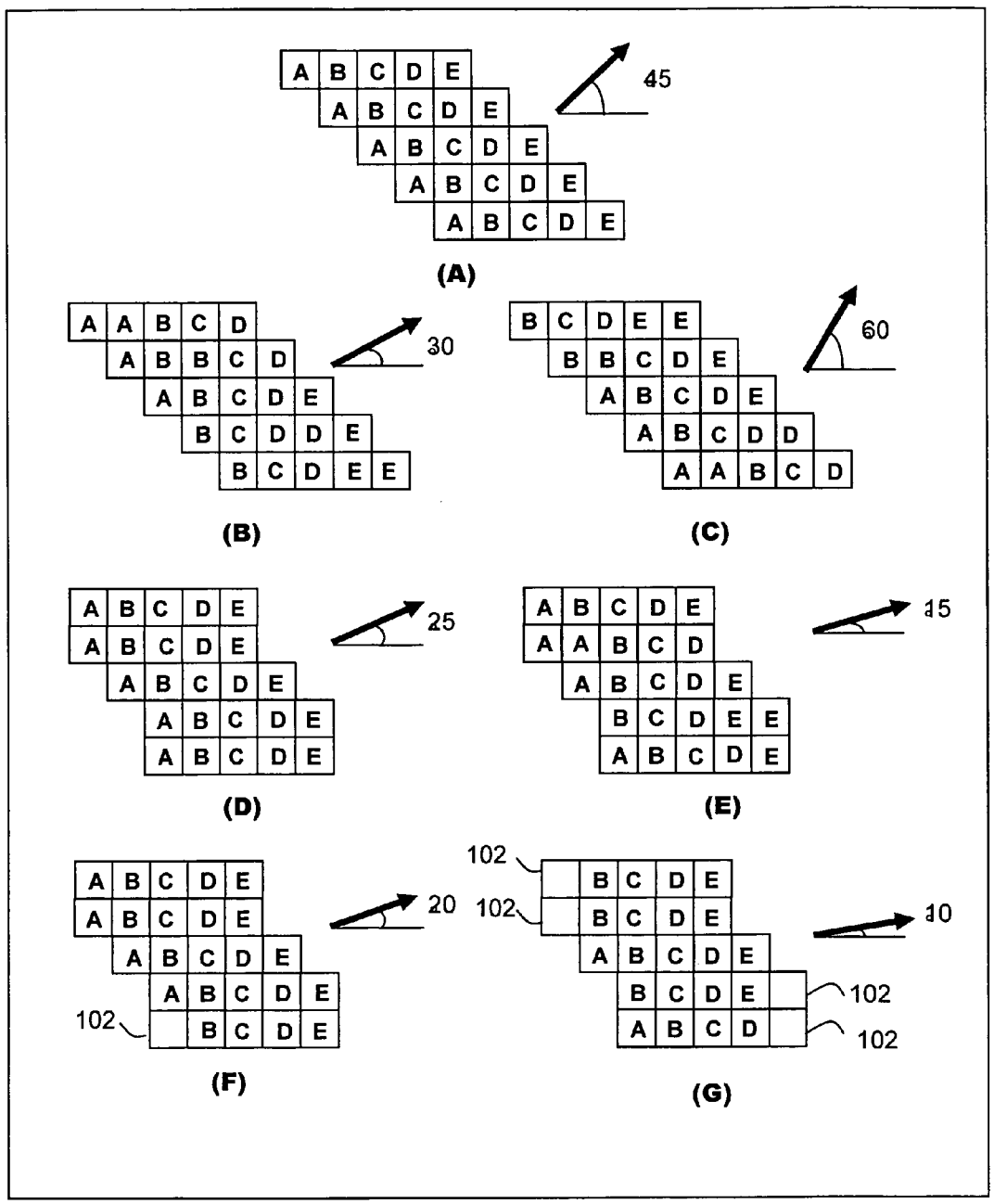
FIG. 12 is a view for explaining another embodiment of the present invention, in which the number of transducer elements varies from group to group.

In FIG. 12, the sub array is composed of 5×5 transducer elements. FIG. 12 (A) shows a sub array shape (which is the same as the shape shown in FIGS. 5, 6(b), and 7) when the beam scanning direction is 45 degrees. Each group is composed of a series of transducer elements arranged orthogonally with respect to the beam scanning direction, and each series of transducer elements includes 5 transducer elements. FIG. 12(B) shows a sub array shape when the beam scanning direction is 30 degrees. FIG. 12(C) shows a sub array shape when the beam scanning direction is 60 degrees. Although the sub arrays shown in FIGS. 12 (B) and (C) have the same shape as that shown in FIG. 12(A), the sub arrays shown in FIGS. 12 (B) and (C) include a plurality of non-linear groups. FIG. 12(D) shows a sub array shape when the beam scanning direction is 25 degrees. In FIG. 12(D), a plurality of groups are identical in the number of transducer elements forming the group and the group shape. Meanwhile, FIG. 12(E) shows a sub array shape when the beam scanning direction is 15 degrees. Although the sub array shown in FIG. 12(E) has the same shape as the sub array shown in FIG. 12(D), these sub arrays have different grouping patterns. FIG. 12(F) shows a sub array shape when the beam scanning direction is 20 degrees. Although the sub array shown in FIG. 12(F) has the same shape as the sub array shown in FIG. 12(D), one ineffective transducer element 102 is included within the sub array shown in FIG. 12(F). FIG. 12(G) shows a sub array shape when the beam scanning direction is 10 degrees. Although the sub array shown in FIG. 12(G) has the same shape as the sub array shown in FIG. 12(E), 4 ineffective transducer elements 102 are included within the sub array shown in FIG. 12(G). In this manner, the position and the number of ineffective transducer elements are variably set in accordance with the beam scanning direction.

Regardless of which sub array shape of those shown in FIGS. 11 and 12 is adopted, a plurality of sub arrays can be closely coupled with each other.

Figure 13:
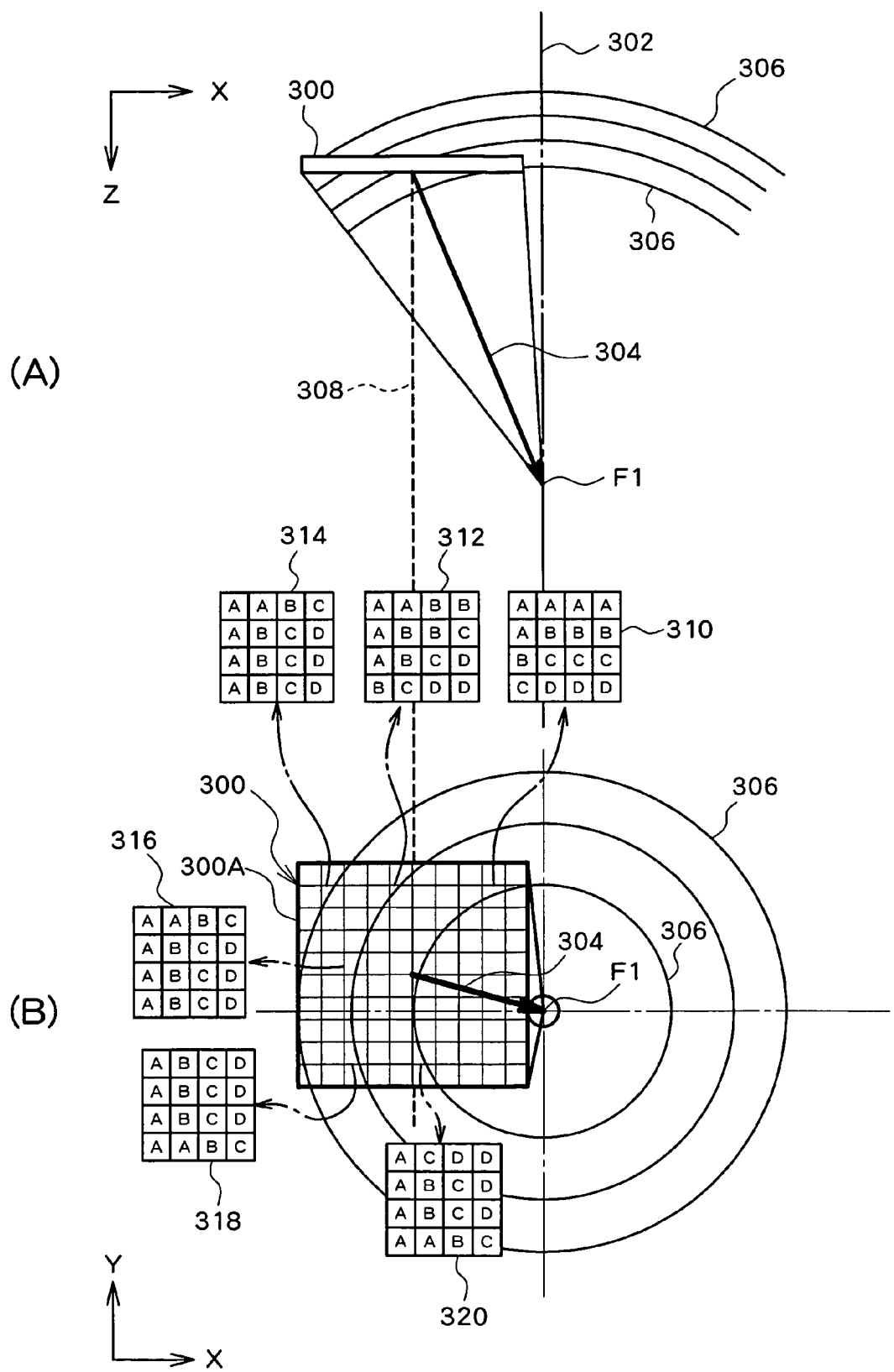
FIG. 13 is a view for explaining an example grouping pattern defined when the beam scanning angle is small at close focus.
Figure 14:
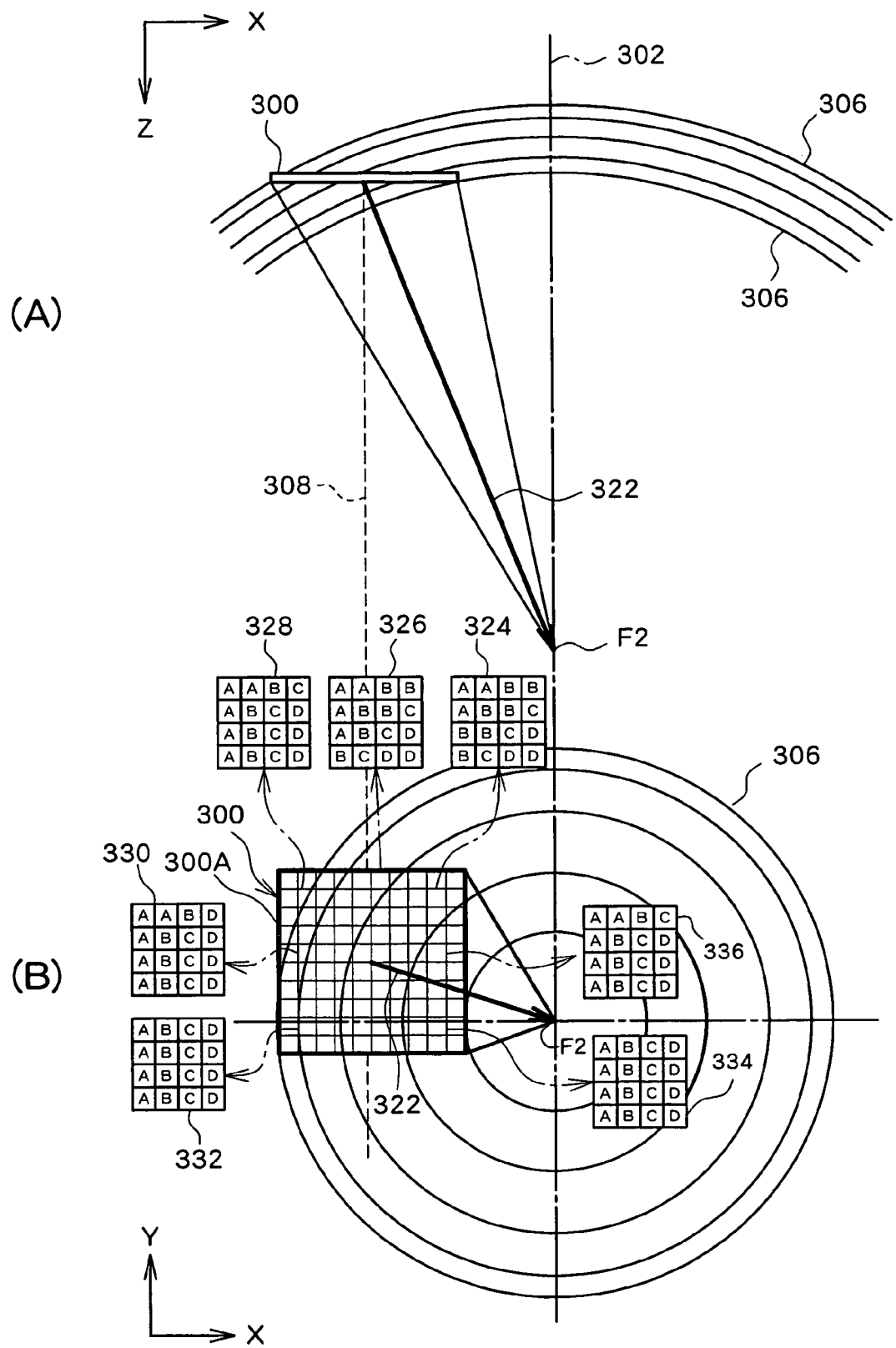
FIG. 14 is a view for explaining an example grouping pattern defined when the beam scanning angle is small at far focus.
Figure 15:
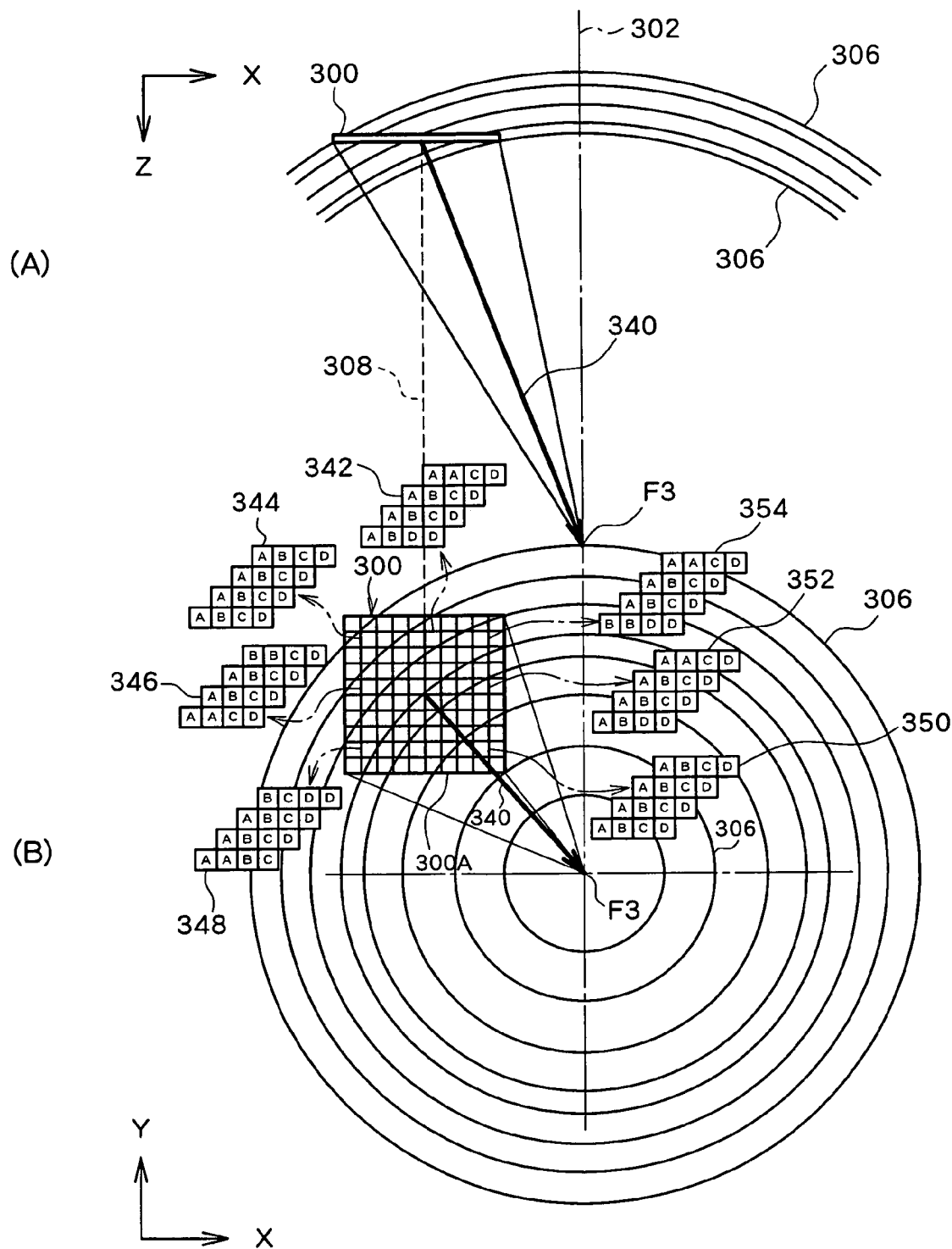
FIG. 15 is a view for explaining an example grouping pattern defined when the beam scanning angle is large at far focus.

Referring now to FIGS. 13 to 15, control in particular consideration of the depth of the focal point will be described in detail.

In this embodiment, the sub array shape is changed in accordance with the beam address (particularly the beam scanning direction) and simultaneously the grouping pattern is individually defined for each sub array in accordance with the beam address, the focal point depth, and the sub array position. More specifically, the sub array shape and the grouping pattern are optimized such that the acoustic distances between respective transducer elements forming each group and the focal point can be made as equal as possible.

FIG. 13(A) shows a plane (XZ plane) which is vertical to the array transducer plane and FIG. 13(B) shows a horizontal plane (XY plane) which is parallel with the array transducer plane. This similarly applies to the cases shown in FIGS. 14 and 15. The X and Y directions correspond to the arrangement direction of the transducer elements, and the Z direction, which is a vertical direction, is orthogonal to the X and Y directions. Reference numeral 302 indicates a vertical axis parallel to the Z axis, which passes through the focal point F1. Reference numeral 304 indicates a transmission beam represented with the center 308 of the array transducer 300 being the origin (a starting point). The transmission beam 304 is directed to the focal point F1. Further, reference numeral 306 indicates an equidistant plane (a wave surface which is a sphere). Ideally, a plurality of transducer elements forming each group are arranged on the equidistant plane. In FIG. 13(B), each cell of the array transducer 300 represents a sub array 300A which is composed of 4×4 transducer elements (see reference numerals 310 to 320, which will be described below).

When the angle defined between the beam direction and the horizontal axis (the X axis in this example) is small and the focal point F1 is defined at a position of relatively small depth as in the example shown in FIG. 13, for example, different grouping patterns 310 to 320 are defined for each sub array on the array transducer 300 in accordance with the position of each sub array, as shown in FIG. 13(B). Specifically, although the sub arrays are of identical shape, a more suitable grouping pattern is defined for each sub array in view of the phase alignment on the unit of each group. In other words, the form of each group and the number of elements forming each group are optimized. When, from the state shown in FIG. 13 described above, the angle defined between the beam scanning direction and the horizontal axis somewhat increases and the depth of the focal point F2 increases as in the case of FIG. 14, grouping patterns 324 to 336 are set for the respective sub arrays as shown in FIG. 14(B). In this case, however, the rectangular shape of each sub array remains unchanged. Further, when, from the state shown in FIG. 14 described above, the angle in the scanning direction increases such that the angle of beam scanning direction is approximately 45 degrees with respect to two orthogonal horizontal axes while the depth of the focus point F3 substantially remains as shown in FIG. 15, the shape of each sub array changes from a rectangular shape to a parallelogram shape, and simultaneously, grouping patterns 342 to 354 are set for the respective sub arrays in accordance with the position of each sub array. The change of the sub array shape is performed in accordance with the conditions shown in FIG. 10 or a simplified version thereof. For example, in the simplified version, only the sub array shapes corresponding to the beam scanning directions of 0 degrees, 45 degrees, 90 degrees, 135 degrees, 180 degrees, 225 degrees, 270 degrees, and 315 degrees shown in FIG. 10 may be used.

As described above, the sub array shape is dynamically variable in accordance with the beam scanning direction. Then, based on the sub array shape which is defined, the grouping pattern is also variably and dynamically defined for each sub array in accordance with the beam scanning direction. In this case, it is desirable to previously compute a set of the best grouping patterns for the whole array transducer with regard to each pair of the beam address and the focal depth and to store, in the table, the switching patterns which can achieve the best grouping patterns. In other words, it is desirable to achieve a structure which allows the optimum switching pattern to be obtained instantaneously from the beam address and the depth of the focal point by referring to the table. As a result of such switching, a plurality of sub arrays are formed on the array transducer and simultaneously the grouping pattern is defined for each sub array. Here, the beam scanning route within the three-dimensional space can be defined as desired. In general, the beam is scanned in a first direction to form a scanning plane, and then the scanning plane is scanned in a second direction.

With the above structure, the optimum grouping pattern is defined for each sub array with reference to the positional relationship between the focal point and a plurality of transducer elements forming a group. Consequently, the channel reduction can be achieved and simultaneously a preferable beam profile can be obtained, which further achieves an advantage of enhancing the quality of an ultrasonic image. In other words, desirable image quality can be obtained while the device structure can be simplified.

Although the preferred embodiments of the present invention have been described using specific terms, such description is for illustrative purposes only, and it is to be understood that modifications and variations may be made without departing from the spirit or scope of the appended claims.

What is claimed is:

1. An ultrasound diagnosis apparatus, comprising:
   an array transducer composed of a plurality of transducer elements for forming an ultrasonic beam which is to be scanned two-dimensionally;
   a switching section which is connected to the array transducer, the switching section defining a plurality of sub arrays with respect to the array transducer and defining a plurality of groups, each being composed of one or a plurality of transducer elements, with respect to each sub array;
   a transmitter section which is connected to the array transducer via the switching section, for generating a group transmission signal for each group; and
   a receiver section which is connected to the array transducer via the switching section, for processing a reception signal of each group which is output from the switching section, wherein:
   the switching section defines a grouping pattern individually for each sub array on the basis of a position of each sub array in the array transducer, a beam address, and a depth of focal point; and
   the switching section dynamically changes the grouping pattern defined for each sub array so as to equalize acoustic distances between the plurality of transducer elements forming each group and the focal point when scanning the ultrasonic beam.

2. An ultrasound diagnosis apparatus according to claim 1, wherein
   the switching section has a function of distributing and outputting the group transmission signal to a plurality of transducer elements forming the corresponding group and a function of summing a plurality of reception signals from a plurality of transducer elements forming each group and generating a group reception signal for each group.

3. An ultrasound diagnosis apparatus comprising:
   an array transducer composed of a plurality of transducer elements for forming an ultrasonic beam which is to be scanned two-dimensionally;
   a switching section which is connected to the array transducer, the switching section defining a plurality of sub arrays with respect to the array transducer in accordance with a beam address and a depth of focus point and defining, with respect to each sub array, a plurality of groups each being composed of one or a plurality of transducer elements in accordance with a position of each sub array;
   a transmitter section which is connected to the array transducer via the switching section, for generating a group transmission signal for each group; and
   a receiver section which is connected to the array transducer via the switching section, for processing a reception signal of each group which is output from the switching section; wherein
   the switching section dynamically changes a grouping pattern defined for each sub to equalize acoustic distances between the plurality of transducer elements forming each group and the focal point when scanning the ultrasonic beam.

4. An ultrasound diagnosis apparatus according to claim 3, wherein
   the switching section changes the sub array shape defined for each sub array in accordance with the beam scanning direction on a horizontal plane which is orthogonal to a vertical center axis of the array transducer.

* * * * *